US012753385B2

(12) United States Patent
Kim et al.

(10) Patent No.: US 12,753,385 B2
(45) Date of Patent: Oct. 6, 2026

(54) COMPOSITION FOR INDUCING DIRECT CROSS DIFFERENTIATION OF SOMATIC CELL INTO MOTOR NEURON, AND METHOD FOR USING SAME

(71) Applicant: UNIST (ULSAN NATIONAL INSTITUTE OF SCIENCE AND TECHNOLOGY), Ulsan (KR)

(72) Inventors: Jeong Beom Kim, Ulsan (KR); Hyun Ah Lee, Ulsan (KR)

(73) Assignee: UNIST (ULSAN NATIONAL INSTITUTE OF SCIENCE TECHNOLOGY), Daejeon (KR)

( * ) Notice: Subject to any disclaimer, the term of this patent is extended or adjusted under 35 U.S.C. 154(b) by 860 days.

(21) Appl. No.: 18/009,443

(22) PCT Filed: Jun. 9, 2020

(86) PCT No.: PCT/KR2020/007461

§ 371 (c)(1),
(2) Date: Dec. 9, 2022

(87) PCT Pub. No.: WO2021/251513

PCT Pub. Date: Dec. 16, 2021

(65) Prior Publication Data

US 2023/0340405 A1 Oct. 26, 2023

(51) Int. Cl.

| | |
|---|---|
| ***C12N 5/0793*** | (2010.01) |
| ***A61K 35/30*** | (2015.01) |
| ***A61K 38/17*** | (2006.01) |
| ***A61P 25/28*** | (2006.01) |
| ***C12N 15/86*** | (2006.01) |

(52) U.S. Cl.

CPC ............ *C12N 5/0619* (2013.01); *A61K 35/30* (2013.01); *A61K 38/1709* (2013.01); *A61P 25/28* (2018.01); *C12N 15/86* (2013.01); *C12N 2501/998* (2013.01); *C12N 2503/02* (2013.01); *C12N 2506/1307* (2013.01); *C12N 2740/15043* (2013.01)

(58) Field of Classification Search

None

See application file for complete search history.

(56) References Cited

U.S. PATENT DOCUMENTS

| | | | | |
|---|---|---|---|---|
| 10,801,010 | B2 * | 10/2020 | Kim | G01N 33/5058 |
| 2015/0023927 | A1 | 1/2015 | Eggan et al. | |
| 2016/0046905 | A1 | 2/2016 | Inoue et al. | |
| 2019/0224335 | A1 * | 7/2019 | Aprikyan | A61P 43/00 |
| 2020/0115678 | A1 | 4/2020 | Nuopponen et al. | |

FOREIGN PATENT DOCUMENTS

| | | | | |
|---|---|---|---|---|
| CN | 106170543 | A | 11/2016 | |
| CN | 106350521 | A | 1/2017 | |
| KR | 10-2013-0030303 | A | 3/2013 | |
| KR | 10-2017-0037929 | A | 4/2017 | |
| WO | WO-2013025963 | A2 * | 2/2013 | A61K 35/30 |
| WO | 2017044853 | A1 | 3/2017 | |

OTHER PUBLICATIONS

Lee, et al., Elife 9 (2020): e52069. (Year: 2020).*
Xu, et al., Cell & Bioscience 10.1 (2020): 116. (Year: 2020).*
Son, et al., Cell stem cell 9.3 (2011): 205-218. (Year: 2011).*
Abernathy, et al. Cell stem cell 21.3 (2017): 332-348. (Year: 2017).*
Saraswathy, et al., Concepts and Techniques in Genomics and Proteomics (2011): CH 4.2 Cosmid vectors (Year: 2011).*
López-González, et al., Archives of medical research 43.1 (2012): 1-10. (Year: 2012).*
Letchuman, et al., eneuro 9.6 (2022). (Year: 2022).*
International Search Report issued in corresponding International Patent Application No. PCT/KR2020/007461 dated Mar. 8, 2021.
Son et al., "Conversion of Mouse and Human Fibroblasts into Functional Spinal Motor Neurons," Cell Stem Cell, 9: 205-218 (2011).
Kim et al., "Direct reprogramming of mouse fibroblasts to neural progenitors," PNAS, 108 (19): 7838-7843 (2011).
R. McDougal et al. "3D-printer visualization of neuron models" Methods published: Jun. 30, 2015; 9 pages.
K. Meyer et al. "Direct conversion of patient fibroblasts demonstrates non-cell autonomous toxicity of astrocytes to motor neurons in familial and sporadic ALS" PNAS; Jan. 14, 2014; vol. 111; No. 2; pp. 829-832.
Qi-lie Zhang et al. "Modeling the phenotype of spinal muscular atrophy by the direct conversion of human fibroblasts to motor neurons" Impact Journals Oncotarget; 2017, vol. 8, (No. 7): pp. 10945-10953.
Jie Zheng et al. "A combination of small molecules directly reprograms mouse fibroblasts into neural stem cells" Biochemical and Biophysical Research Communications; May 4, 2016; 21 pages.

* cited by examiner

*Primary Examiner* — Maria Marvich
*Assistant Examiner* — Brendan Thomas Tinsley
(74) *Attorney, Agent, or Firm* — Morgan, Lewis & Bockius LLP

(57) ABSTRACT

Provided are a composition for inducing direct conversion from a somatic cell into a motor neuron, a motor neuron induced through direct conversion by introducing the composition into a somatic cell, a pharmaceutical composition for the prevention or treatment of nervous system disease and injury, a cell therapeutic agent, a composition for screening for a drug for the prevention or treatment of nervous system disease and injury, and a 3D printing biomaterial composition for constructing artificial tissue.

12 Claims, 7 Drawing Sheets

COMPOSITION FOR INDUCING DIRECT CROSS DIFFERENTIATION OF SOMATIC CELL INTO MOTOR NEURON, AND METHOD FOR USING SAME

TECHNICAL FIELD

The present disclosure relates to a composition for inducing direct conversion from a somatic cell into a motor neuron, a motor neuron induced through direct conversion by introducing the composition into a somatic cell, a pharmaceutical composition for the prevention or treatment of nervous system disease and injury, a cell therapeutic agent, a composition for screening for a drug for the prevention or treatment of nervous system disease and injury, and a 3D printing biomaterial composition for constructing artificial tissue.

BACKGROUND ART

Existing methods for differentiation into motor neurons using embryonic stem cells and dedifferentiated stem cells require establishing embryonic stem cells by destroying embryos, or undergoing differentiation into motor neurons after somatic cells are reprogrammed into dedifferentiated stem cells, to construct cells. In addition, conventional methods may raise ethical issues since embryonic stem cells are used. Also, when dedifferentiated stem cells are used, a differentiation step requires time, costs, and efforts, while having low efficiency, and the artificial control of differentiation capacity is not easy, and thus, these methods are inefficient. In addition, it is difficult to obtain a sufficient number of cells required for drug metabolism and toxicity verification at the in-vitro level, and, in the application stage of cell therapy for regenerating motor neuron functions, these is a high possibility that teratoma derived from undifferentiated cells is formed, and thus, there were safety issues in using the cells.

To eliminate the risk of teratoma formation as described above, research is being conducted on direct conversion of somatic cells into somatic cells of other lineages or multipotent stem cells without going through pluripotent stem cells. However, it is difficult to verify detailed mechanisms since a great number of genes are used to induce such a cell reprogramming process, and thus, findings have so far been insufficient. In addition, even though dedifferentiation technology has been established, technically simple and highly efficient methods must be continuously developed for actual therapeutic application, and all of these developed technologies have to be evaluated in terms of efficiency and safety, thus being restrictive. In addition, there has yet been no known method for producing motor neurons by expressing only a few genes from somatic cells.

Therefore, as a result of having conducted research on a method for direct conversion from a somatic cell into a motor neuron, the inventors of the present disclosure confirmed that, when ectopic expression of a transcription factor of a specific gene was induced in somatic cells, the somatic cells could be effectively induced into neurons, thus completing the present disclosure.

DETAILED DESCRIPTION OF THE DISCLOSURE

Technical Problem

One aspect relates to a composition for inducing direct conversion from a somatic cell into a motor neuron, the composition including at least one selected from the group consisting of: (1) at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; (2) a nucleic acid molecule encoding the at least one protein; and (3) a vector into which the nucleic acid molecule is introduced.

Another aspect relates to a method for direct conversion from a somatic cell into a motor neuron, the method including a step of bringing or inserting, into contact with or into a somatic cell, a composition including at least one selected from the group consisting of: (1) at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; (2) a nucleic acid molecule encoding the at least one protein; and (3) a vector into which the nucleic acid molecule is introduced.

Another aspect relates to a motor neuron induced through direct conversion by introducing, into a somatic cell, at least one selected from the group consisting of: (1) a nucleic acid molecule encoding at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; and (2) a vector into which the nucleic acid molecule is introduced.

Another aspect relates to a pharmaceutical composition and cell therapeutic agent for the prevention or treatment of nervous system disease and injury, the compositions including a motor neuron induced through direct conversion as an active ingredient.

Another aspect relates to a composition for screening for a drug for the prevention or treatment of nervous system disease and injury, the composition including a motor neuron induced through direct conversion as an active ingredient.

Another aspect relates to a 3D printing biomaterial composition for constructing artificial tissue for treating nervous system disease and injury.

Another aspect relates to a method for preventing or treating nervous system disease and injury, the method including a step of administering the composition for inducing direct conversion or the motor neuron induced through direct conversion to a subject in need thereof.

Technical Solution

To achieve the above objects, one aspect provides a composition for inducing direct conversion from a somatic cell into a motor neuron, the composition including at least one selected from the group consisting of: (1) at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; (2) a nucleic acid molecule encoding the at least one protein; and (3) a vector into which the nucleic acid molecule is introduced.

Another aspect provides a method for direct conversion from a somatic cell into a motor neuron, the method including a step of bringing or inserting, into contact with or into a somatic cell, a composition including at least one selected from the group consisting of: (1) at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; (2) a nucleic acid molecule encoding the at least one protein; and (3) a vector into which the nucleic acid molecule is introduced.

Another aspect provides a motor neuron induced through direct conversion by introducing, into a somatic cell, at least one selected from the group consisting of: (1) a nucleic acid molecule encoding at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; and (2) a vector into which the nucleic acid molecule is introduced.

Another aspect provides a pharmaceutical composition and cell therapeutic agent for the prevention or treatment of nervous system disease and injury, the compositions including a motor neuron induced through direct conversion as an active ingredient.

Another aspect provides a composition for screening for a drug for the prevention or treatment of nervous system disease and injury, the composition including a motor neuron induced through direct conversion as an active ingredient.

Another aspect provides a 3D printing biomaterial composition for constructing artificial tissue for treating nervous system disease and injury.

Another aspect provides a method for preventing or treating nervous system disease and injury, the method including a step of administering the composition for inducing direct conversion or the motor neuron induced through direct conversion to a subject in need thereof.

Hereinafter, the present disclosure will be described in more detail.

The term "direct conversion" refers to a process of inducing conversion between mature (differentiated) cells of completely different cell types in higher organisms (Kim, J. et al, Neurobiol. 22, 778-784, 2012). Unlike conventional techniques that require reprogramming of somatic cells into induced pluripotent stem cells (iPSCs) and re-differentiating the iPSCs into target cells, the present disclosure differs in that direct conversion into target cells is induced without going through the stage of induced pluripotent stem cells. Currently, direct conversion is recognized for its potential applications in disease modeling, new drug development, and the like, and thus, is known to be a technique that can also be applied to gene therapy, regenerative medicine, and the like.

The composition for inducing direct conversion, according to one aspect, may include at least one selected from the group consisting of: (1) at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; (2) a nucleic acid molecule encoding the at least one protein; and (3) a vector into which the nucleic acid molecule is introduced.

The composition may include: any one or more proteins selected from an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; and/or a nucleic acid molecule encoding any one or more of the proteins. For example, the composition may include OCT4, LHX3, ISL1, NKX6.1, NGN2, or SOX11, and may include a combination selected from: OCT4 and LHX3; OCT4 and ISL1, OCT4 and NKX6.1, OCT4 and NGN2; OCT4 and SOX11, OCT4, LHX3, and ISL1, OCT4, LHX3, and NKX6.1; OCT4, LHX3, and NGN2; and OCT4, LHX3, and SOX11.

The nucleic acid molecule encoding at least one of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-Box 11 (SOX11) protein may be used in the state of being inserted into a vector expressing an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-Box 11 (SOX11) protein, the vector including a nucleic acid molecule encoding the at least one protein.

The term "vector" as used herein is an expression vector capable of expressing a target protein in a suitable host cell, and may refer to a gene delivery system including essential regulatory factors operably linked so that a gene insert is expressed.

The vector of the present disclosure includes a signal sequence or a reader sequence for membrane targeting or secretion, in addition to expression regulatory factors such as a promoter, an operator, an initiation codon, a termination codon, a polyadenylation signal, and an enhancer, and may be variously constructed according to the purpose of use. The promoter of the vector may be constructive or inductive. In addition, the expression vector includes a selectable marker for selecting a host cell containing the vector, and a replicable expression vector includes an origin of replication. The vector may be self-replicating or integrated into host DNA.

In a specific embodiment, by introducing, into somatic cells, a nucleic acid molecule encoding at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein, or a vector into which the nucleic acid molecule is introduced, direct conversion from the somatic cells into motor neurons was confirmed.

In addition, in the composition of the present disclosure, a transcription factor capable of inducing direct conversion into a motor neuron can be introduced via a vector, and the vector that may be used in the present disclosure may be, for example, at least one vector selected from the group consisting of a plasmid vector, a cosmid vector, a viral vector, a lentiviral vector, a retrovirus vector, a human immunodeficiency virus (HIV) vector, a murineleukemia virus (MLV) vector, an avian sarcoma/leukosis (ASLV) vector, a spleen necrosis virus (SNV) vector, a rous sarcoma virus (RSV) vector, a mouse mammary tumor virus (MMTV) vector, an adenovirus vector, an adeno-associated virus vector, a Herpes simplex virus vector, and an episomal vector.

The octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein may be provided in the form of a nucleic acid molecule encoding at least one of the proteins or a vector into which the nucleic acid molecule is introduced. The octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein may include all octamer-binding transcription factor 4 (OCT4) proteins, LIM homeobox 3 (LHX3) proteins, ISL LIM homeobox 1 (ISL1) proteins, NK6 homeobox 1 (NKX6.1) proteins, neurogenin 2 (NGN2) proteins, and SRY-box 11 (SOX11) proteins that are derived from mammals such as humans, horses, sheep, pigs, goats, camels, antelopes, and dogs. In addition, the octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein that may be used in the present disclosure may include not only a protein having the amino acid sequence of wild type thereof, but also a variant of at least one protein selected from the group consisting of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein (e.g., subtypes of each protein).

The variants of the octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein refer to proteins that have sequences different from natural amino acid sequences of the octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein by deletion, insertion, non-conservative or conservative substitution, or a combination thereof of one or more amino acid residues in the natural amino acid sequences thereof, and retain the intrinsic biological functions of wild-type proteins. The variant may be a functional equivalent that exhibits the same biological activity as a wild-type protein, or a variant in which the physicochemical properties of the protein are modified as needed, and may be a variant with enhanced structural stability in physical and chemical environments or increased physiological activity.

The octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein, or variants thereof may be isolated from nature, or recombinantly or synthetically produced (non-naturally occurring).

In addition, a nucleic acid encoding at least one of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein is a nucleotide sequence encoding wild-type or the variant form of the at least one protein as described above, and may have one or more bases mutated by substitution, deletion, insertion, or a combination thereof, and may be isolated from nature or produced using a chemical synthesis method. A nucleic acid having a nucleotide sequence encoding at least one of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein may be single-stranded or double-stranded, and may be a DNA molecule (genome, cDNA) or an RNA (mRNA) molecule.

In a specific embodiment, by introducing direct conversion factors, i.e., OCT4 or OCT4 and LHX3 into fibroblasts selected as a representative example of somatic cells, via lentivirus, and causing ectopic expression of the factors, the fibroblasts were directly converted into motor neurons. It was also confirmed through reverse transcription PCR of the induced motor neurons that motor neuron markers different from those of fibroblasts before the induction of a direct conversion factor were expressed in the induced motor neurons.

The term "somatic cell" may refer to all cells excluding reproductive cells, and somatic cells may be derived from or isolated from, for example, mammals such as humans, horses, sheep, pigs, goats, camels, antelopes, and dogs. In addition, the composition of the present disclosure may induce direct conversion from a somatic cell into a motor neuron, and the somatic cell may be, but is not limited to, at least one selected from the group consisting of a fibroblast, an epithelial cell, a muscle cell, a nerve cell, a hair cell, a hair root cell, a hair follicle cell, an oral epithelial cell, a somatic cell extracted from urine, a gastric mucosal cell, a goblet cell, a G cell, a B cell, a pericyte, an astrocyte, a blood cell, a neural stem cell, a hematopoietic stem cell, an umbilical cord blood stem cell, and a mesenchymal stem cell. In a specific embodiment of the present disclosure, fibroblasts were used as the somatic cells.

The term "motor neuron" is a type of neurons constituting the nervous system, and refers to a neuron that transmits a signal from the central nervous system such as the spinal cord, to an effector such as muscle or gland to enable the same to operate. Also, the term "induced motor neuron" may refer to, for example, a motor neuron induced from a somatic cell through direct conversion, according to one aspect.

In a specific embodiment, the method for direct conversion may include the steps of: culturing a somatic cell in a medium; transfecting the cultured somatic cell with a vector into which at least one of an octamer-binding transcription factor 4 (OCT4) gene, an LIM homeobox 3 (LHX3) gene, an ISL LIM homeobox 1 (ISL1) gene, an NK6 homeobox 1 (NKX6.1) gene, a neurogenin 2 (NGN2) gene, and an SRY-box 11 (SOX11) gene is inserted; and culturing the transfected somatic cell under culture conditions capable of inducing direct conversion. In addition, the method for direct conversion may further include a step of transfecting a somatic cell with at least one of an octamer-binding transcription factor 4 (OCT4) gene, an LIM homeobox 3 (LHX3) gene, an ISL LIM homeobox 1 (ISL1) gene, an NK6 homeobox 1 (NKX6.1) gene, a neurogenin 2 (NGN2) gene, and an SRY-box 11 (SOX11) gene.

The medium used in the culturing of the somatic cell includes all media commonly used in the art for culturing somatic cells. The medium used for culture generally includes a carbon source, a nitrogen source, and a trace element component. In a specific embodiment of the present disclosure, a medium containing protamine sulphate was used, but the present disclosure is not limited thereto.

In addition, the culture conditions capable of inducing direct conversion of a somatic cell may include media and/or general culture conditions commonly used in the art to induce direct conversion of somatic cells.

Through the introduction of the composition for inducing direct conversion, into a somatic cell, the ectopic expression of direct conversion factors such as octamer-binding transcription factor 4 (OCT4), LIM homeobox 3 (LHX3), ISL LIM homeobox 1 (ISL1), NK6 homeobox 1 (NKX6.1), neurogenin 2 (NGN2), and SRY-box 11 (SOX11) may be induced. Ectopic expression means expression in a tissue or a cell in which a gene is not originally expressed, or expression at time different from the original expression time. According to the method of the present disclosure, a motor neuron may be effectively produced from a somatic cell.

The motor neuron induced by the method and composition according to one aspect may not express a marker derived from the original cell and may express a marker which is expressed only in a motor neuron. In one aspect, to obtain a motor neuron induced through direct conversion, direct conversion may be induced using a composition including at least one of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein. By using a composition including: a nucleic acid molecule encoding at least one of an octamer-binding transcription factor 4 (OCT4) protein, an LIM homeobox 3 (LHX3) protein, an ISL LIM homeobox 1 (ISL1) protein, an NK6 homeobox 1 (NKX6.1) protein, a neurogenin 2 (NGN2) protein, and an SRY-box 11 (SOX11) protein; or a vector into which the nucleic acid molecule is introduced, direct conversion into motor neurons was confirmed. In addition, in a specific embodiment, when a composition including a nucleic acid molecule encoding an octamer-binding transcription factor 4 (OCT4) protein or a vector having the nucleic acid molecule introduced thereinto further included a nucleic acid molecule encoding an LIM homeobox 3 (LHX3) protein or a vector having the nucleic acid molecule introduced thereinto, direct conversion from somatic cells into motor neuron by the composition was confirmed. In addition, the motor neuron induced through direct conversion may be provided by: any one or more proteins selected from the octamer-binding transcription factor 4 (OCT4) protein, the LIM homeobox 3 (LHX3) protein, the ISL LIM homeobox 1 (ISL1) protein, the NK6 homeobox 1 (NKX6.1) protein, the neurogenin 2 (NGN2) protein, and the SRY-box 11 (SOX11) protein that are included in the composition; and/or a nucleic acid molecule encoding any one or more of the proteins.

The term "prevention" refers to all actions that prevent the corresponding disease by eliminating the etiology of nervous system disease and injury or detecting the same early.

The term "treatment" refers to all actions that alleviate or beneficially change symptoms due to nervous system disease and injury, by the composition of the present disclosure.

The nervous system disease and injury that can be prevented or treated may be, for example, at least one selected from the group consisting of spinal cord injury, Parkinson's disease, stroke, amyotrophic lateral sclerosis, motor nerve injury, traumatic peripheral nerve injury, ischemic brain injury, neonatal hypoxic ischemic brain injury, cerebral palsy, epilepsy, intractable epilepsy, Alzheimer's disease, congenital metabolic nervous system disease, and traumatic brain injury, but the present disclosure is not limited thereto, and may include all diseases and/or pathological symptoms caused by hypofunction, loss, and/or abnormal functioning of the nervous system.

The composition may further include at least one known active ingredient that has the effect of preventing or treating nervous system disease and injury, along with the induced motor neuron.

The composition may further include a pharmaceutically acceptable additive. In this regard, the pharmaceutically acceptable additive may be, for example, starch, gelatinized starch, microcrystalline cellulose, lactose, povidone, colloidal silicon dioxide, calcium hydrogen phosphate, lactose, mannitol, syrup, gum arabic, pregelatinized starch, corn starch, powdered cellulose, hydroxypropyl cellulose, Opadry, starch sodium glycolate, carnauba wax, synthetic aluminum silicate, stearic acid, magnesium stearate, aluminum stearate, calcium stearate, sucrose, or the like. The pharmaceutically acceptable additive according to the present disclosure may be included in an amount of 0.1 parts by weight to 90 parts by weight with respect to the composition.

The composition may be administered orally or parenterally in various dosage forms during actual clinical administration, and may be formulated using commonly used diluents or excipients such as fillers, extenders, binders, wetting agents, disintegrating agents, and surfactants. As suitable formulations known in the art, those disclosed in the literature (Remington's Pharmaceutical Science, the latest, Mack Publishing Company, Easton PA) may be used. A carrier, an excipient and a diluent that may be included in the composition may be lactose, dextrose, sucrose, oligosaccharides, sorbitol, mannitol, xylitol, erythritol, maltitol, starch, acacia gum, alginates, gelatin, calcium phosphate, calcium silicate, cellulose, methyl cellulose, microcrystalline cellulose, polyvinylpyrrolidone, water, methylhydroxy benzoate, propylhydroxy benzoate, talc, magnesium stearate, mineral oil, and the like.

A suitable dose of the composition may vary depending on conditions and body weights of individuals, severity of disease, types of drugs, administration route, and administration time, but may be appropriately selected by those of ordinary skill in the art. To obtain desired effects, the motor neuron induced through direct conversion according to the present disclosure may be administered in an amount of, for example, about 1,000 cells/time to about 10,000 cells/time, about 1,000 cells/time to about 100,000 cells/time, about 1,000 cells/time to about 1,000,000 cells/time, about 1,000 cells/time to about 10,000,000 cells/time, about 1,000 cells/time to about 100,000,000 cells/time, about 1,000 cells/time to about 1,000,000,000 cells/time, or about 1,000 cells/time to about 10,000,000,000, based on an adult patient weighing 70 kg, and may be administered once a day to several times a day at regular intervals, or may be administered several times at regular intervals.

The composition may be administered to a subject via various routes. All administration methods may be predicted, and may be, for example, oral administration, rectal or intravenous administration, and intramuscular or subcutaneous injection, and the composition may be administered via any route that enables application to the skin.

The term "individual" refers to a subject with nervous system disease and injury requiring treatment and, more particularly, refers to mammals such as humans, non-human primates, mice, rats, dogs, cats, horses, and cows.

In one aspect, the composition may be used alone for the prevention or treatment of nervous system disease and injury, or may be used in combination with surgery, radiotherapy, hormone treatment, chemotherapy, and methods using a biological response modifier. A pharmaceutical composition including the motor neuron induced through direct conversion may further include a HB9 protein.

The term "cell therapeutic agent" refers to a therapeutic agent using autologous, allogenic or xenogenic cells to recover the function of a tissue, and refers to a therapeutic agent used to suppress cancer. The cell therapeutic agent including the motor neuron induced through direct conversion as an active ingredient may be used as a cell therapeutic agent for the prevention or treatment of nervous system disease and injury.

The cell therapeutic agent may further include a pharmaceutically acceptable carrier. The pharmaceutically acceptable carrier may be, for example, saline, sterile water, Ringer's solution, buffered saline, dextrose solution, maltodextrin solution, glycerol, ethanol, human serum albumin (HSA), and a mixture of two or more of these ingredients, and, if necessary, other general additives such as an antioxidant, buffer, and a bacteriostatic agent may be added.

The cell therapeutic agent may further include, for example, a diluent, a dispersing agent, a surfactant, a binder, and a lubricant, and may be formulated into an injectable formulation, for example, an aqueous solution, a suspension, or an emulsion.

The composition for screening for a drug for the prevention or treatment of nervous system disease and injury may be effectively used to screen for a therapeutic agent for nervous system disease and injury, as a method of identifying the responsiveness of the motor neuron induced through direct conversion of the present disclosure in the presence or absence of a therapeutic candidate substance for nervous system disease and injury. For example, the motor neuron induced through direct conversion according to one aspect may be used to evaluate toxicity or efficacy of a candidate substance as a cell important for recovery or treatment of nervous system disease and injury.

The toxicity may be evaluated according to a method of determining toxicity commonly used in the art, for example, in the presence or absence of a therapeutic candidate substance or based on $IC_{50}$ of the motor neuron induced through direct conversion according to the present disclosure. In addition, the efficacy may be evaluated in the presence or absence of a therapeutic candidate substance, according to a method capable of confirming that the motor neuron induced through direct conversion according to the present disclosure has the effect of treating nervous system disease and injury, such as the regeneration of damaged nerves.

The 3D printing technology relates to an output technology for printing a three-dimensional (3D) solid material, and the 3D printing biomaterial composition refers to biocompatible polymers, natural polymers, biomolecules, bioactive substances, and cells that have the characteristics of biomimetics, small tissues, and autonomous self-assembly.

According to one aspect, through layered manufacturing of the motor neuron induced through direct conversion into a desired shape or pattern, it is possible to construct artificial tissue for treating nervous system disease and injury, which can be widely used in the field of regenerative therapy.

Redundant description will be omitted in consideration of the complexity of the present specification. Unless otherwise defined herein, terms have meanings commonly used in the technical field to which the present disclosure pertains.

Advantageous Effects of Disclosure

When a composition of one aspect is used, differentiation from a somatic cell into a motor neuron can be efficiently induced through the expression of direct conversion inducers without going through the pluripotency stage of dedifferentiated stem cells. Thus, nervous system disease and injury can be effectively prevented and treated using the composition. In addition, an induced motor neuron of one aspect can be used as a therapeutic pharmaceutical composition for treating nervous system disease and injury that are known as conventional intractable diseases and a 3D printing biomaterial composition for constructing artificial tissue, and thus can be widely used in the field of regenerative therapy.

MODE OF DISCLOSURE

Figure 1A:
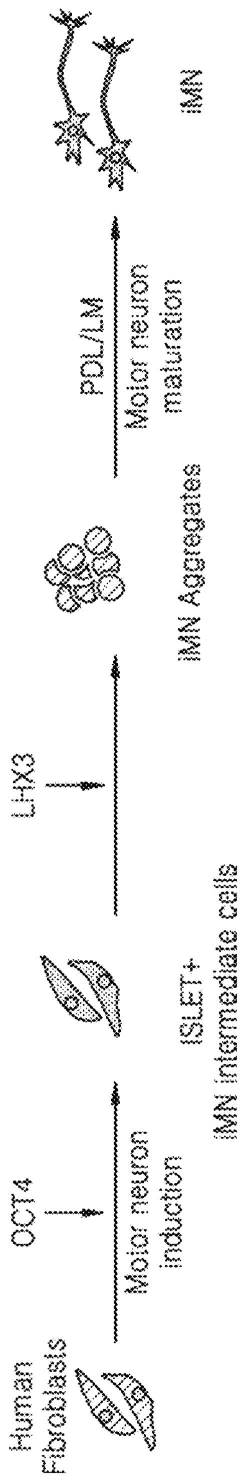
FIG. 1A is a schematic view illustrating a process of inducing direct conversion from fibroblasts into motor neurons.

Hereinafter, the present disclosure will be described in detail with reference to experimental examples and examples to aid the understanding of the present disclosure. However, the following experimental examples and examples are illustrative purposes only and are not intended to limit the scope of the present disclosure. The experimental examples and examples of the present disclosure are provided to completely explain the present disclosure to those of ordinary skill in the art.

EXPERIMENTAL EXAMPLES AND EXAMPLES

<Experimental Example 1> Cloning and Packaging of Lentiviral Plasmid

Transcription factors (OCT4 and LHX3) were amplified by polymerase chain reaction (PCR) using cDNA of HepG2. Subsequently, the transcription factors were introduced into a lentiviral vector and confirmed by sequencing. The packaging of lentivirus was performed by adding a lentiviral transfer plasmid, a packaging plasmid (psPAX2), and an envelope plasmid (VSV-G) in a ratio of 3:2:1 by using an X-tremeGENE 9 DNA transfection reagent (Roche, 06365787001). 293T cells at a confluency of 50% were treated with a mixture of which the total volume was made to 200 μl by adding DMEM, and transformed for 48 hours. The cell medium was centrifuged at 80,000 g in an ultracentrifuge for 1.5 hours, and then the centrifuged lentivirus pellet was diluted in 1 ml of DMEM (Gibco, 10313-021) and was used for transformation.

<Experimental Example 2> Cell Culture Medium and Production of Induced Motor Neurons (iMNs)

Skin fibroblasts were dispensed at a density of $3\times10^4$ cells on gelatin-coated 6-well plates in a 10% FBS culture medium. After one day, the fibroblasts were transfected with a pMX retroviral vector expressing each of OCT4, LHX3, ISL1, NKX6.1, NGN2, and SOX11, and pMX retroviral vectors expressing combinations of: OCT4 and LHX3; OCT4 and ISL1, OCT4 and NKX6.1; OCT4 and NGN2; OCT4 and SOX11, OCT4, LHX3, and ISL1, OCT4, LHX3, and NKX6.1; OCT4, LHX3, and NGN2; and OCT4, LHX3, and SOX11 in a medium containing 6 μg/ml of protamine sulphate, thereby producing induced motor neurons. Thereafter, the viral supernatants were removed, followed by replacement with new media. After the fibroblasts were transfected with each vector, the produced iMNs were plated onto a PDL/laminin-coated 4-well plate, which is a motor neuron differentiation medium. After plating, the cells were cultured and the neuronal cell population was mechanically separated, and mature iMNs were picked or trypsinized on the gelatin-coated plates to be subcultured.

<Experimental Example 3> RNA Extraction and cDNA Synthesis

Total RNA of the cell lysate was extracted with RiboEX (Geneall, 301-001). RNA extraction was performed according to the manufacturers protocol. cDNA was synthesized with M-MuLV-reverse transcriptase (NEB, M0253L) by adding 500 ng of RNA and oligo-dT primer to a total of 20 μl of the reaction mixture.

<Experimental Example 4> RT-PCR Analysis

Reverse transcription polymerase chain reaction (RT-PCR) was performed at 58° C. for 35 cycles using Taq polymerase (Invitrogen, 10342-020) and a primer pair. The PCR product was subjected to gel electrophoresis on a 1% agarose gel at 100 V for 25 minutes, and for motor neuron marker genes and motor neuron progenitors/neuroectoderm markers, the experiment was repeated three times, followed by normalization to the housekeeping gene Gapdh. Gene expression was measured and analyzed by the Ct value calculation method, and all experiments were performed according to the manufacturer's instructions.

<Experimental Example 5> Immunofluorescence Staining

Cells were fixed with 4% paraformaldehyde (Tech & Innovation, BPP-9004) at room temperature for 10 minutes. The fixed cells were washed three times with Dulbecco's phosphate-buffered saline (DPBS, Corning, 21-031-CV). Subsequently, the cells were permeabilized by treatment with DBPS containing 0.1% Triton X-100 (Sigma, T9284) at room temperature for 10 minutes. The cells were washed three times with DPBS, followed by reacting with DPBS containing 4% FBS at room temperature for 1 hour, to block non-specific binding. Subsequently, the cells were cultured with primary antibodies at room temperature for 1 hour, and then washed three times with DPBS containing 0.05% Tween-20 (Sigma, P7949). Thereafter, the samples were treated with secondary fluorescent antibodies and incubated in the dark for 1 hour. If double staining is required, an additional blocking step was performed for 30 minutes before treatment with primary antibodies according to the above process.

<Experimental Example 6> Microarray Analysis

By using microarray analysis, the overall gene expression profiles of fibroblasts, induced motor neuron intermediate cells (iMN intermediate cells) as fibroblasts after OCT4 infection, induced motor neurons (Mock iMN) produced only through OCT4 infection, and induced motor neurons (LHX3_iMN) produced by treatment with LHX3 after OCT4 infection were analyzed and compared with one another. Total RNA was isolated using an RNeasy mini kit (Qiagen) according to the manufacturers instructions. The sample was hybridized with Affymetrix array. The sample was normalized through calculation using an RNA (Robust Multi-array Analysis) algorithm. Data processing and graphics were performed using internally developed Matlab. Hierarchical clustering of genes and samples was carried out through a one minus correlation metric and the unweighted average distance (UPGMA) linkage method.

<Experimental Example 7> Production of Spinal Cord Injury Model and Transplantation of Induced Motor Neurons A spinal cord injury model was constructed using an air punching device for injuring the chest spine level 9 (T9) of the spinal cord of 6-week-old male rats. One week after injury, harvested iMNs were labeled with Dil and injected at a concentration of $1\times10^5$ iMNs/rat into the chest spine level 8 (T8) and the chest spine level 10 (T10) of the spinal cord through a stereotaxic method. Water and food were regularly fed to the rats and the bladder of each rat was massaged for urination. The animal testing was approved by the Animal Facility and the IBR Committee of the Ulsan National Institute of Science and Technology. The animal experimental process was based on the guidelines of the National Institute of Health for animal studies.

Example 1. Induction of Induced Motor Neurons (iMNs) by Direct Conversion Factor To induce motor neurons, skin fibroblasts were seeded in a culture medium and transformed with OCT4, which is a transcription factor that causes induction into motor neurons, by using a lentivirus expression system for 24 hours, thereby producing induced motor neuron intermediate cells (iMN intermediate cells). Subsequently, LHX3 was additionally introduced into the cells by using a lentivirus expression system, thereby producing induced motor neurons, or induced motor neurons into which LHX3 was not introduced were produced. Thereafter, skin tissue was attached to gelatin-coated culture dishes, and the neurons were cultured for use. The experimental process is schematically illustrated in FIG. 1A, and the histological morphology of cells obtained by three-dimensionally culturing the induced motor neurons is illustrated in FIG. 1B.

Figure 1B:
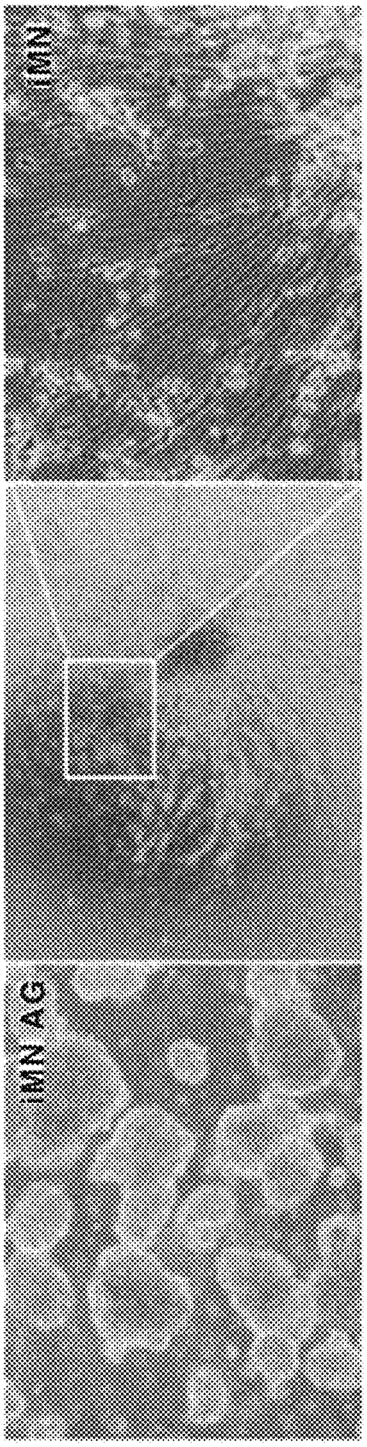
FIG. 1B illustrates the results of confirming the histological morphology of induced motor neurons produced by three-dimensional culture.

As illustrated in FIG. 1B, it was confirmed that aggregates were formed about 20 days after transformation with lentivirus, and the typical morphology of motor neurons appeared on day 5 after three-dimensional culture thereof. Through the above results, it was confirmed that, when the ectopic expression of OCT4 and LHX3 was induced by treating fibroblasts, which are somatic cells, therewith, motor neurons could be effectively produced. In particular, it was confirmed that the motor neurons induced by the above process exhibited characteristic morphology that appears in actual motor neurons.

Example 2. Induction of Induced Motor Neurons (iMNs) by Direct Conversion Factor Experiments were carried out to: confirm whether, when direct conversion into motor neurons is induced by introducing, into somatic cells, one of the direct conversion factor genes and combinations of two or more thereof, direct conversion efficiency is effectively shown; and confirm the direct conversion efficiencies of the combinations of direct conversion factors. Induced motor neurons were produced using one of the direct conversion factor genes and combinations thereof under the same condition as in Experimental Example 2, and the results of confirming the expression of HB9, which is a motor neuron marker for direct conversion, in the produced motor neurons are illustrated in FIG. 2A, and the results of measuring the direct conversion efficiencies of one of the genes and combinations thereof are illustrated in FIG. 2B.

Figure 2:
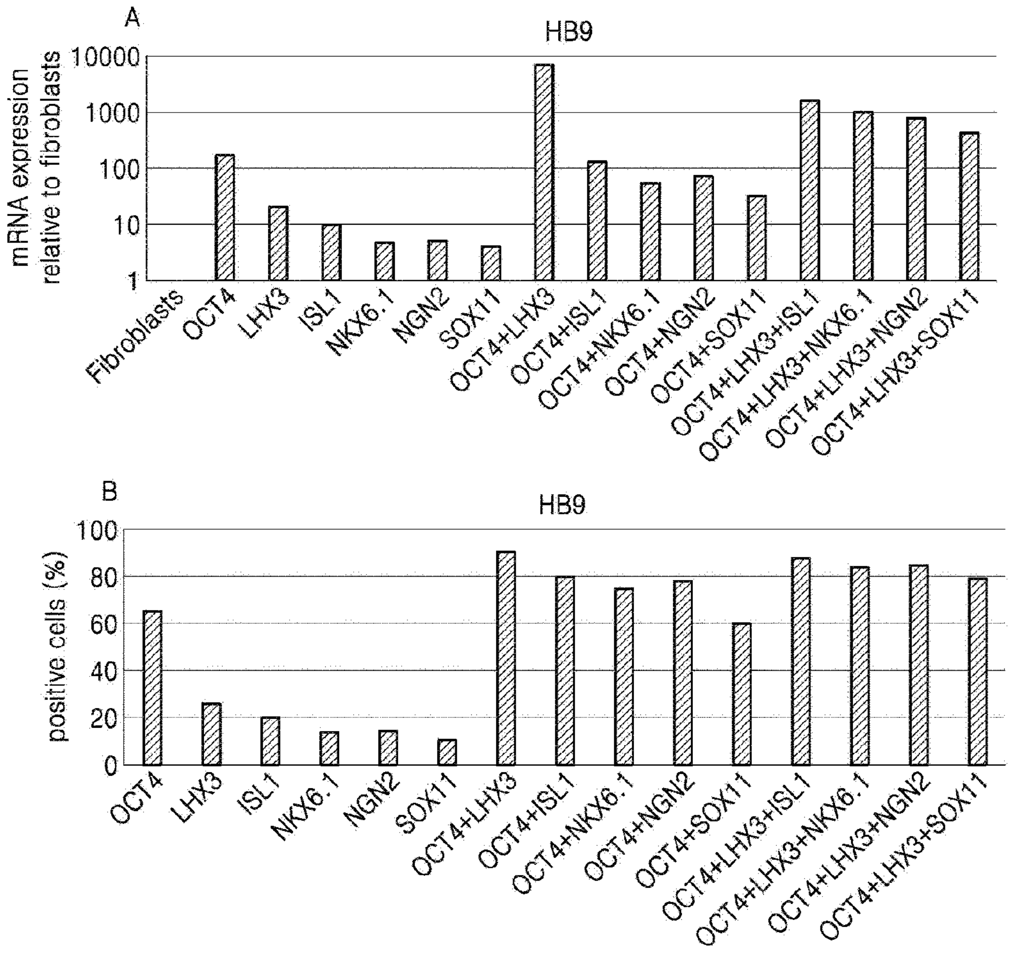
FIG. 2 illustrates graphs showing: the results of confirming HB9 gene expression in motor neurons induced using one of the direct conversion factor genes or a combination thereof (FIG. 2A); and the results of confirming the direct conversion efficiency of the motor neurons induced using the factor(s) (FIG. 2B).

As illustrated in FIG. 2A, it was confirmed that the expression of HB9, which is a motor neuron marker, decreased in the order of OCT4, LHX3, ISL1, NKX6.1, NGN2, and SOX11, and it was confirmed that the expression level of H59, which is a motor neuron marker, increased 500 times or more that of fibroblasts in the combinations of factors: OCT4 and LHX3; OCT4, LHX3, and ISL1; OCT4, LHX3, and NKX6.1; OCT4, LHX3, and NGN2; and OCT4, LHX3, and SOX11. In addition, as illustrated in FIG. 2B, it was confirmed that, in the case of OCT4 from among the direct conversion factor genes, cells expressing the HB9 protein, which is a motor neuron marker, had the highest direct conversion efficiency. It was also confirmed that all the combinations of the direct conversion factors exhibited an efficiency of 60% or more, from which it was confirmed that the direct conversion efficiency was higher than that in the case of single factors.

Example 3. Confirmation of Characteristics of Motor Neurons Induced Through Direct Conversion To confirm whether the motor neurons (iMNs) induced according to Examples 1 and 2 exhibit not only the morphology but also the characteristics of actual motor neurons, western blotting and RT-PCR analysis were carried out and at the same time, immunofluorescence staining was performed. Experiments were carried out according to the methods disclosed in Experimental Examples 4 to 6, and the immunofluorescence staining results are illustrated in FIG. 3, the results of confirming gene markers expressed through western blotting are illustrated in FIG. 4, and the results of confirming differences in relative gene expression levels shown in induced motor neurons compared to fibroblasts, which are originating cells, are illustrated in FIG. 5.

Figure 3:
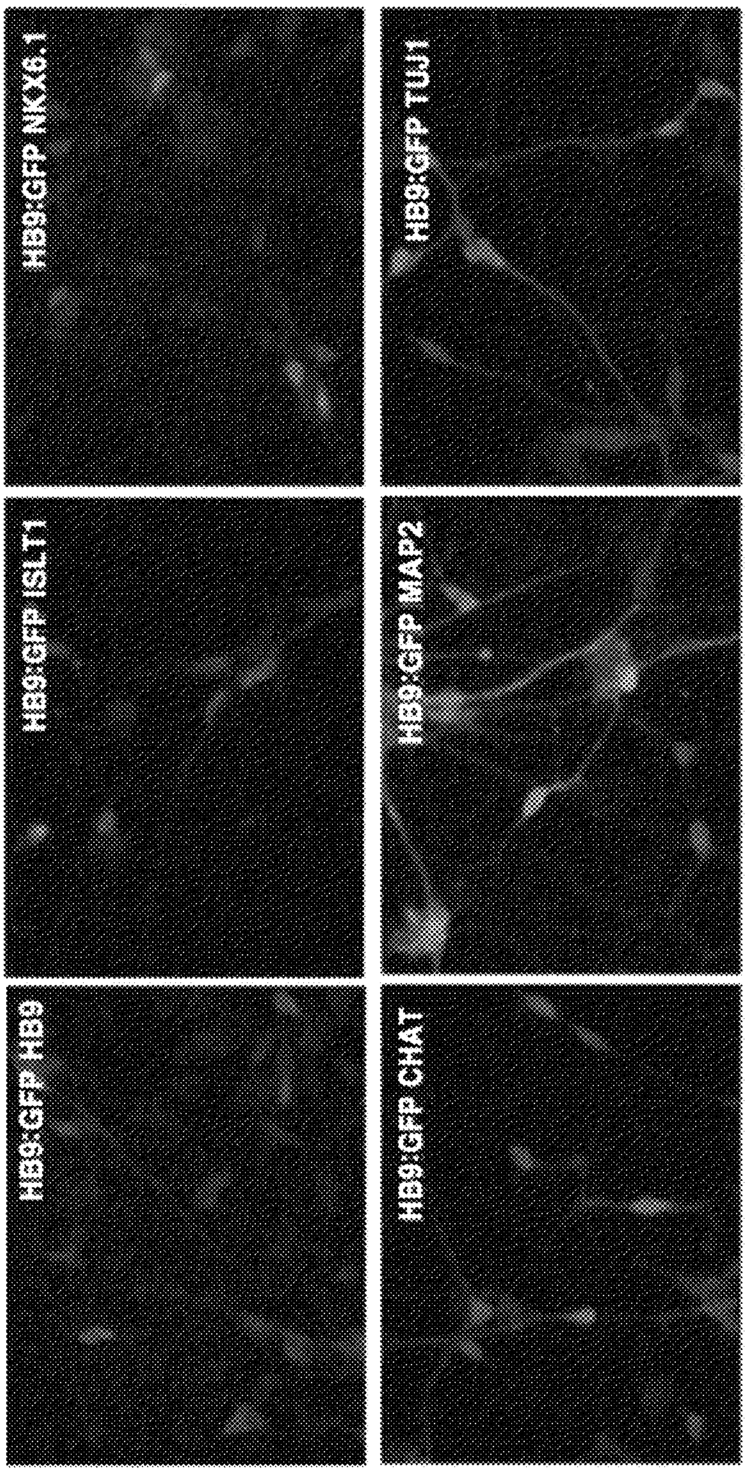
FIG. 3 illustrates the results of performing immunofluorescence staining on induced motor neurons.
Figure 4:
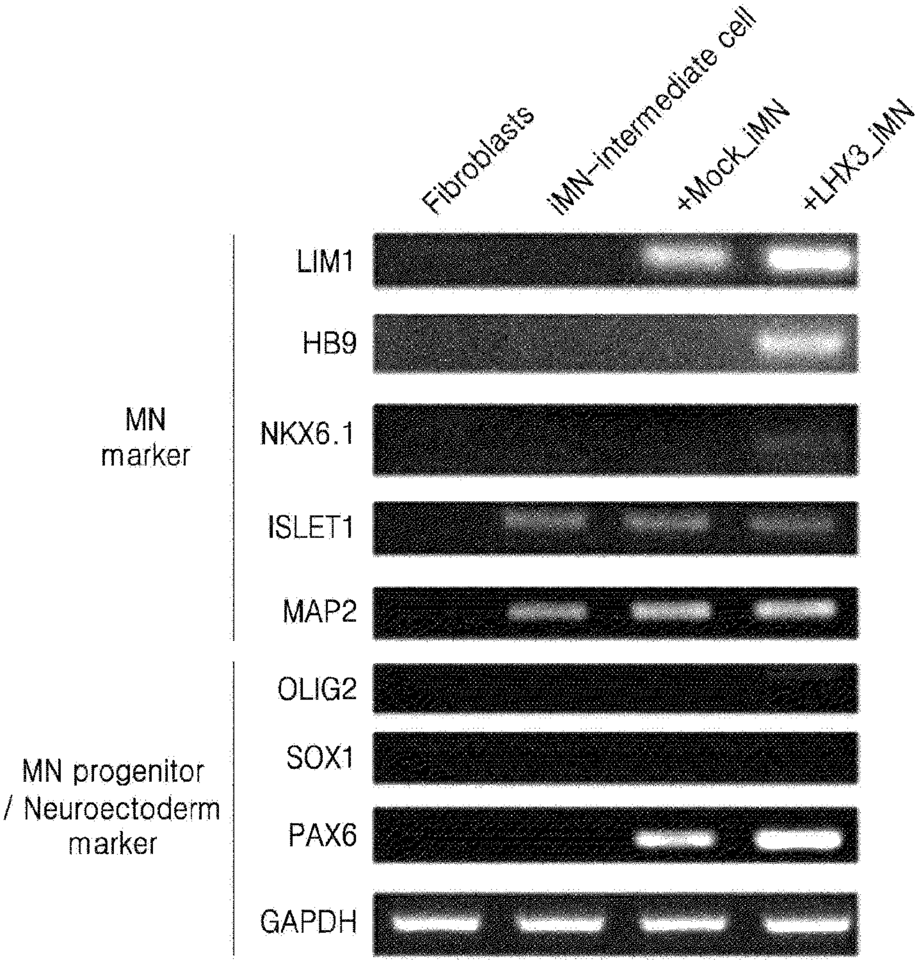
FIG. 4 illustrates the results of confirming motor neuron markers expressed in induced motor neurons (induced motor neuron intermediate cells, induced motor neurons produced by OCT4 infection, and induced motor neurons treated with LHX3 after OCT4 infection).

As illustrated in FIG. 3, it was confirmed that motor neuron markers, i.e., HB9, ISLT1, NKX6.1, MAP2 and TUJ1 markers, which are not expressed in fibroblasts, were strongly expressed in the produced iMNs. In addition, as illustrated in FIG. 4, it was confirmed that the expression of ISLT1 and MAP2 markers was shown in induced motor neuron intermediate cells (iMN intermediate cells), and a group of motor neurons induced only with OCT4 (+Mock+iMN) expressed ISLT1 and MAP2 and further expressed LIM1. It was confirmed that a group of motor neurons induced by further introducing LHX3 (+LHX3_iMN) expressed all of LIM1, HB9, ISLT1, NKX6.1, and MAP2.

Figure 5:
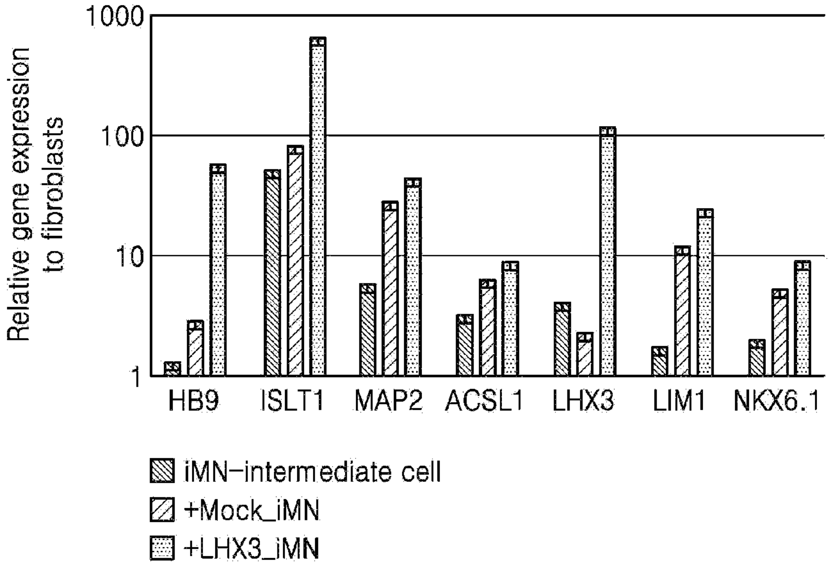
FIG. 5 illustrates the results of confirming differences in relative gene expression levels shown in induced motor neurons compared to fibroblasts, which are originating cells.

In addition, as illustrated in FIG. 5, it was confirmed that the expression of ISLT1 was remarkably increased in the induced motor neuron intermediate cells, and it was also confirmed that the expression of ISLT1, MAP2, and LIM1 increased 10 times or more in the Mock_iMN group in which motor neurons were induced only with OCT4. In the LHX3_iMN group in which motor neurons were induced by further introducing LHX3, all of the expression levels of LIM1, HB9, ISLT1, NKX6.1, SCSL1, and MAP2 increased about 10 times or more.

From the above results, it was confirmed that the produced iMNs exhibited not only the morphology but also the characteristics of actual motor neurons in which motor neuron markers are clearly expressed. However, as illustrated in FIGS. 3 and 4, it was confirmed that the expression patterns of motor neuron markers that can be confirmed according to the combination of direct conversion transcription factors used could be slightly different.

Thus, taking the above results together, it was confirmed that motor neurons induced from fibroblasts were the same as actual motor neurons, from which it was confirmed that motor neurons could be efficiently induced through the methods disclosed in the examples.

Example 4. Confirmation of Nerve Injury Treatment Effect Via Administration of iMNs in Spinal Cord Injury Animal Model An experiment was performed to confirm whether the motor neurons produced according to the examples exhibit a therapeutic effect when administered to a spinal cord injury animal model. The experimental method was the same as that used in Experimental Example 7, and the results of confirming the results of comparison in the nerve injury treatment effect of the group administered with iMN and the mouse spinal cord injury model to which additionally induced iMNs were administered in combination with HB9, with control mice, by the BBB score, which is an index for confirming the degree of motor function recovery, are illustrated in FIG. 6A, and the results of confirming spinal cord parts by H&E staining are illustrated in FIG. 6B.

Figure 6:
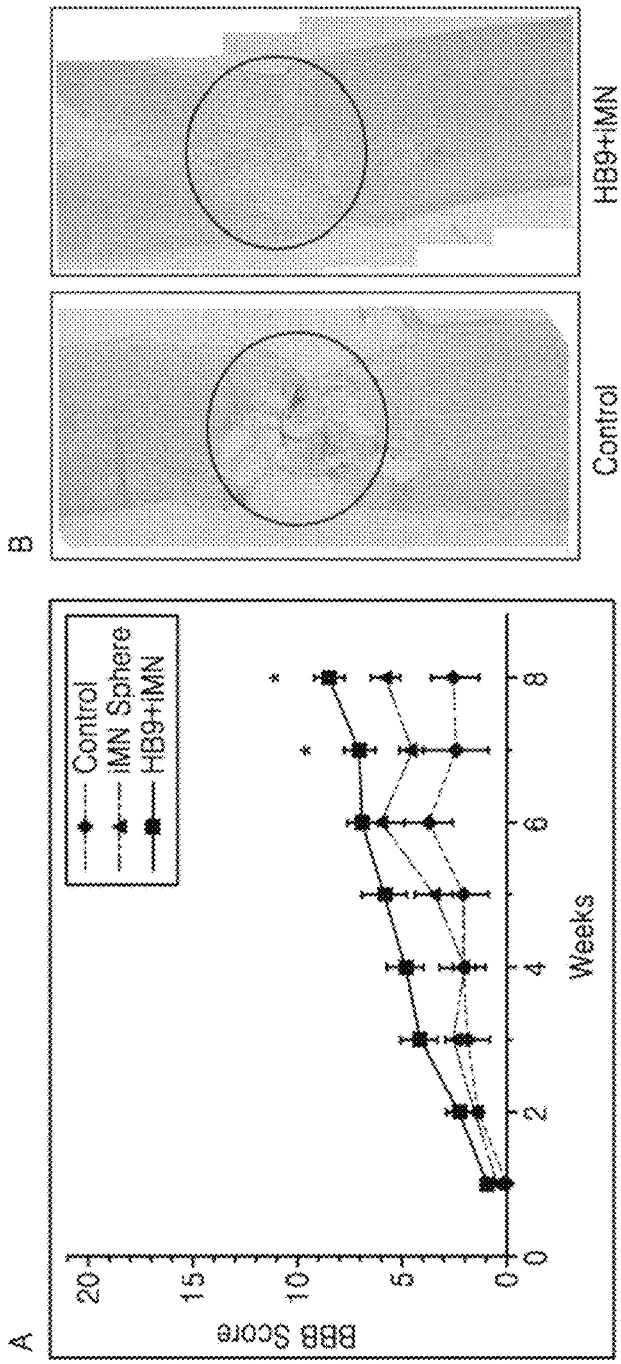
FIG. 6 illustrates the results of confirming the effect of treating nerve injury in mouse spinal cord injury models, compared to control mice, by the BBB score, which is an index for confirming the degree of motor function recovery (FIG. 6A), and illustrates the results obtained by performing H&E staining on spinal cord parts (FIG. 6B).

As illustrated in FIG. 6A, it was confirmed that, compared to the control, the degree of motor function recovery remarkably increased over time from five weeks after injection in the iMN-injected group. It was also confirmed that the degree of motor function recovery steadily increased from one week after injection in the group administered with IMNs in combination with HB9, and in particular, the motor function was remarkably recovered from three weeks. In addition, as illustrated in FIG. 6B, it was confirmed that, compared to the control, damaged tissue in an injured part of the spinal cord was significantly reduced when the induced iMNs were administered in combination with HB9.

Through the above results, it was confirmed that, when induced motor neurons were administered, nervous system disease and injury could be effectively treated, thus confirming the possibility of being used as a therapeutic composition capable of preventing or treating the disease and the like.

The invention claimed is:

1. A method for direct conversion from a somatic cell into a motor neuron in vitro, the method comprising a step of bringing into contact with a somatic cell or of inserting into a somatic cell, a composition comprising:

at least one direct conversion factor selected from the group consisting of an OCT4 protein, a nucleic acid molecule encoding the OCT4 protein operably linked to a promoter, and a vector into which the nucleic acid molecule encoding the OCT4 protein is introduced; and at least one additional direct conversion factor selected from the group consisting of a LHX3 protein, a nucleic acid molecule encoding the LHX3 protein, and a vector into which the nucleic acid molecule encoding the LHX3 protein is introduced, wherein the somatic cell is selected from the group consisting of a fibroblast, an epithelial cell, an oral epithelial cell, a hematopoietic stem cell, an umbilical cord blood stem cell, and a mesenchymal stem cell, and the vector comprises a viral vector selected from the group consisting of a lentiviral vector, a retrovirus vector, a human immunodeficiency virus (HIV) vector, a murineleukemia virus (MLV) vector, an adenovirus vector, and an adeno-associated virus vector.

2. The method of claim 1, wherein the composition comprises:

at least one further direct conversion factor selected from the group consisting of at least one protein selected from the group consisting of ISL1, NKX6.1, NGN2, and SOX11, a nucleic acid molecule encoding the at least one protein selected from the group consisting of ISL1, NKX6.1, NGN2, and SOX11 operably linked to a promoter, and a vector into which the nucleic acid molecule encoding the at least one protein elected from the group consisting of ISL1, NKX6.1, NGN2, and SOX11 is introduced wherein the somatic cell is selected from the group consisting of a fibroblast, an epithelial cell, an oral epithelial cell, a hematopoietic stem cell, an umbilical cord blood stem cell, and a mesenchymal stem cell, and the vector comprises a viral vector selected from the group consisting of a lentiviral vector, a retrovirus vector, a human immunodeficiency virus (HIV) vector, a murineleukemia virus (MLV) vector, an adenovirus vector, and an adeno-associated virus vector.

3. The method of claim 1, wherein the somatic cell comprises a fibroblast.

4. The method of claim 1, wherein the somatic cell is selected from the group consisting of an epithelial cell, an oral epithelial cell, a hematopoietic stem cell, an umbilical cord blood stem cell, and a mesenchymal stem cell.

5. The method of claim 1, wherein the vector comprises a lentiviral vector.

6. The method of claim 1, the vector comprises a viral vector selected from the group consisting of a retrovirus vector, a human immunodeficiency virus (HIV) vector, a murineleukemia virus (MLV) vector, an adenovirus vector, and an adeno-associated virus vector.

7. The method of claim 1, wherein the at least one additional direct conversion factor comprises the vector into which the nucleic acid molecule encoding the LHX3 protein is introduced, wherein the vector comprises a lentiviral vector.

8. The method of claim 2, wherein the somatic cell comprises a fibroblast.

9. The method of claim 2, wherein the somatic cell is selected from the group consisting of an epithelial cell, an oral epithelial cell, a hematopoietic stem cell, an umbilical cord blood stem cell, and a mesenchymal stem cell.

10. The method of claim 2, wherein the vector comprises a lentiviral vector.

11. The method of claim 2, the vector comprises a viral vector selected from the group consisting of a retrovirus vector, a human immunodeficiency virus (HIV) vector, a murineleukemia virus (MLV) vector, an adenovirus vector, and an adeno-associated virus vector.

12. The method of claim 2, wherein the at least one additional direct conversion factor comprises the vector into which the nucleic acid molecule encoding the LHX3 protein is introduced, wherein the vector comprises a lentiviral vector.

* * * * *